(12) United States Patent
Smyth et al.

(10) Patent No.: US 10,092,660 B2
(45) Date of Patent: Oct. 9, 2018

(54) SOLID COMPOSITIONS FOR PHARMACEUTICAL USE

(75) Inventors: Hugh Smyth, Austin, TX (US); Ibrahim M. El-Sherbiny, El-Mansoura (EG)

(73) Assignee: STC.UNM, Albuquerque, NM (US)

( * ) Notice: Subject to any disclaimer, the term of this patent is extended or adjusted under 35 U.S.C. 154(b) by 17 days.

(21) Appl. No.: 14/113,653

(22) PCT Filed: Apr. 25, 2012

(86) PCT No.: PCT/US2012/034882
§ 371 (c)(1),
(2), (4) Date: Dec. 9, 2013

(87) PCT Pub. No.: WO2012/148953
PCT Pub. Date: Nov. 1, 2012

(65) Prior Publication Data
US 2014/0141094 A1    May 22, 2014

Related U.S. Application Data

(60) Provisional application No. 61/478,699, filed on Apr. 25, 2011.

(51) Int. Cl.
| | | |
|---|---|---|
| *A61K 9/51* | (2006.01) | |
| *A61K 47/48* | (2006.01) | |
| *A61K 9/00* | (2006.01) | |
| *A61K 31/496* | (2006.01) | |

(52) U.S. Cl.
CPC ...... *A61K 47/48923* (2013.01); *A61K 9/0075* (2013.01); *A61K 9/5161* (2013.01); *A61K 31/496* (2013.01)

(58) Field of Classification Search
CPC ... A61K 31/496; A61K 9/0075; A61K 9/5161
See application file for complete search history.

(56) References Cited

U.S. PATENT DOCUMENTS

| | | | |
|---|---|---|---|
| 2002/0061336 A1* | 5/2002 | O'Connor | A61K 9/0021 424/499 |
| 2005/0208122 A1 | 9/2005 | Allen et al. | |
| 2005/0214227 A1 | 9/2005 | Prestrelski et al. | |
| 2008/0031824 A1 | 2/2008 | Smyth et al. | |
| 2008/0038358 A1 | 2/2008 | Steiner et al. | |
| 2008/0124400 A1 | 5/2008 | Liggins et al. | |
| 2009/0117039 A1 | 5/2009 | Richard | |
| 2009/0192576 A1* | 7/2009 | Seifert | A61N 1/0568 607/116 |
| 2009/0203579 A1* | 8/2009 | Defrees | A61K 47/48092 514/1.1 |
| 2009/0238875 A1* | 9/2009 | Noh et al. | 424/487 |
| 2010/0004189 A1 | 1/2010 | Watson et al. | |
| 2010/0081278 A1* | 4/2010 | Hussain | B82Y 10/00 438/666 |
| 2010/0209509 A1* | 8/2010 | Kao | A61K 47/48215 424/486 |
| 2010/0234233 A1 | 9/2010 | Sannino et al. | |

FOREIGN PATENT DOCUMENTS

WO    WO-2012148953    11/2012

OTHER PUBLICATIONS

Sigma "Agar Product Information" Oct. 15, 1996, pp. 1-5.*
Drugs.com "Ciprofloxacin" (https://web.archive.org/web/20110308180137/http://www.drugs.com/ciprofloxacin.html) Apr. 13, 2011, pp. 1-4.*
Berger, J. et al. "Structure and interactions in covalently and ionically crosslinked chitosan hydrogels for biomedical applications" European Journal of Pharmaceutics and Biopharmaceutics 57 (2004) 19-34.*
CDC "Glutaraldehyde" (http://www.cdc.gov/niosh/topics/glutaraldehyde/) accessed Mar. 2, 2016, p. 1-6.*
Sigma 2 (http://www.sigmaaldrich.com/catalog/product/sigma/g9422?lang=en&region=US) accessed Mar. 2, 2015, p. 1-3.*
Bhattarai, N. et al. "PEG-grafted chitosan as an injectable thermosensitive hydrogel for sustained protein release" J Control Release 2005, 103, 609-624.*
Koo, H-J. et al. "Anti-inflammatory evaluation of gardenia extract, geniposide and genipin" Journal of Ethnopharmacology 2006, 103, 496-500.*
Sachse, F. et al. "Anti-inflammatory effects of ciprofloxacin in *S. aureus* Newman induced nasal inflammation in vitro" J. Inflamm. 2008, 5 (11), 1-6.*
Zhao, X. et al. "Stress-relaxation behavior in gels with ionic and covalent crosslinks" Journal of Applied Physics 2010, 107, 06350-1-063509-5.*
Chaudhury, A. et al. "Recent Advancement of Chitosan-Based Nanoparticles for Oral Controlled Delivery of Insulin and Other Therapeutic Agents" AAPS PharmSciTech, vol. 12, No. 1, Mar. 2011, pp. 10-20.*
"Calcium" (https://ods.od.nih.gov/factsheets/Calcium-HealthProfessional/) Nov. 17, 2016, pp. 1-21.*
Zhao, X. et al. "Stress-relaxation behavior in gels with ionic and covalent crosslinks" Journal of Applied Physics 2010, 107, 063509-1-063509-5 (Year: 2010).*
International Search Report & Written Opinion, PCT/US12/34882, dated Jul. 18, 2012.
"International Application Serial No. PCT/US2012/034882, Written Opinion dated Jul. 18, 2012", 3 pgs.
Muzzarelli, Riccardo A, "Genipin-crosslinked chitosan hydrogels as biomedical and pharmaceutical aids", Carbohydrate Polymers 77 (2009) 1-9, (2009), 9 pgs.

* cited by examiner

*Primary Examiner* — Andrew S Rosenthal
(74) *Attorney, Agent, or Firm* — Schwegman Lundberg & Woessner, P.A.

(57) ABSTRACT

The invention relates to solid compositions that may be suitable for administering a therapeutic agent to a subject. The invention also relates to methods of making such solid compositions. The invention further relates to methods of treating a disease, condition, or disorder by administering to a subject such solid compositions.

30 Claims, 12 Drawing Sheets

SOLID COMPOSITIONS FOR PHARMACEUTICAL USE

CROSS-REFERENCE TO RELATED APPLICATIONS

The present application claims the benefit of priority to U.S. Provisional Patent Application No. 61/478,699, filed Apr. 25, 2011, which is incorporated herein by reference as though fully set forth in its entirety.

FIELD OF THE INVENTION

The invention relates to solid compositions that may be suitable for administering a therapeutic agent to a subject. The invention also relates to methods of making such solid compositions. The invention further relates to methods of treating a disease, condition, or disorder by administering to a subject such solid compositions.

BACKGROUND OF THE INVENTION

Infections of the lower respiratory tract are common. These include acute infections, such as pneumonia or bronchitis. These also include chronic infections, such as infections associated with cystic fibrosis or chronic obstructive pulmonary disorder (COPD). These chronic infections affect the lungs and can eventually lead to death.

Administration of antibiotics is known to reduce the rate of lung tissue degradation and thereby enhance the survival rate of those suffering from chronic infections of the lungs and airways. Such antibiotics are typically administered orally or through injection. But these methods involve certain shortcomings. In particular, these methods do not permit specific targeting of the infected areas of the lower respiratory tract. It would be desirable to be able to deliver the antibiotic directly to the infected airways and lungs. In this way, smaller doses could be used, and dosing would occur with less frequency.

Inhalation provides one possible solution to this problem. Yet this poses other problems. For example, if the microparticles are sufficiently small to reach the lung, then the particles are of an ideal size to be eliminated from the lungs via macrophage uptake. Thus, there is a continuing need for solid compositions that can be used to deliver a dose of antibiotic to the lower respiratory tract, including the deep lung, that will substantially resist elimination from the lungs by macrophage uptake.

SUMMARY OF THE INVENTION

In at least one aspect, the invention provides solid compositions comprising a plurality of hydrogel particles, wherein the hydrogel particles each comprise one or more hydrophilic polymers and a therapeutic agent.

In another aspect, the invention provides methods of treating a lower respiratory tract infection, the method comprising insufflating a subject with an effective amount of the solid composition comprising a plurality of hydrogel particles, wherein the hydrogel particles each comprise two or more hydrophilic polymers and a therapeutic agent.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

DETAILED DESCRIPTION

Figure 1:
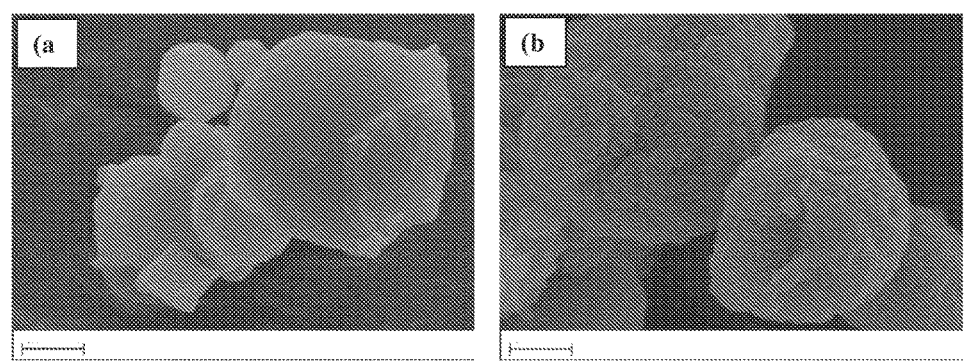
FIG. 1 shows scanning electron micrographs (SEM) for plain microparticles (FIG. 1a) and for ciprofloxacin-loaded microparticles (FIG. 1b). The micrographs were recorded with an EHT of 10.00 kV; WD=21.7 mm (1a) and 21.4 mm (1b); Signal A=SE2; and magnification of 50.00 K X. The bar at the bottom of each of FIGS. 1a and 1b show a distance of 1 μm.

The following section provides a detailed description of various embodiments of the invention. None of these embodiments is intended to serve as a source of substantive limitations on the scope of the claimed subject matter, unless otherwise indicated. The embodiments are provided for illustrative purposes only as examples of embodiments that are within the scope of the invention.

Definitions

As used herein, "a" and "an" refer to one or more of the thing to which they refer.

As used herein, "or" means that one or more of the things recited in a list may be present; it is thus not intended to refer to mutually exclusive alternatives. Thus, the phrase "A or B" implies, for example, that A can be present, that B can be present, and that A and B can both be present.

As used herein, the term "solid composition" refers to a dry powder composition. In some embodiments, the dry powder composition is a composition suitable for administration to a subject via a powder insufflator.

As used herein, "pharmaceutically acceptable salt" refers to salts of a free acid or a free base which are not biologically undesirable, at least at administered quantities, and are generally prepared by reacting the free base with a suitable organic or inorganic acid or by reacting the acid with a suitable organic or inorganic base. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. When an acidic substituent is present, such as —$CO_2H$, there can be formed, for example, an ammonium, morpholinium, sodium, potassium, barium, calcium salt, and the like, for use as a solid composition. When a basic group is present, such as amino or a basic heteroaryl radical, such as pyridyl, there can be formed an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethanesulfonate, picrate and the like. In some embodiments, the same compound can have both basic and acidic groups, and thus can form pharmaceutically acceptable salts with both acidic and basic counterions, respectively. In some embodiments, the acidic or basic counterions can be part of a polymeric chain, such as part of an ionic polymer. Pharmaceutically acceptable acids and bases include those recited in Berge, et al., *J. Pharm. Sci.*, Vol. 66, pp. 1-19 (1977).

As used herein, "free acid" and "free base" refer to compounds or moieties that function as acids or bases in according to the Bronsted-Lowry model of acids and bases. In some embodiments, a compound can be both a free acid and a free base. Ciprofloxacin, for example, includes a basic amine group and an carboxylic acid group. A compound, e.g., a polysaccharide, can be said to have an acidic or basic moiety if it includes, for example, acid or amine groups.

As used herein, the term "hydrophilic polymer" refers to a polymer that has a plurality of functional groups that are charge polarized and capable of functioning as hydrogen bond acceptors or donors. In some embodiments, the hydrophilic polymer is an ionic polymer. As used herein, "ionic polymer" refers to a polymer, such as a polysaccharide, that includes one or more functional groups that can exchange a hydrogen with a free acid or a free base. For example, a polysaccharide that includes one or more carboxylic acid or carboxylate groups is an ionic polymer. The same would apply to a polysaccharide that includes one or more amine or ammonium groups. As used herein, a "anionic polymer" refers to an ionic polymer that includes functional groups that have donated or are capable of donating a hydrogen atom in an aqueous medium. For example, an ionic polymer, such as an alginate, that has one or more carboxylic acid or carboxylate groups can be referred to as an anionic polymer. As used herein, a "cationic polymer" refers to an ionic polymer that includes functional groups that have accepted or are capable of accepting a hydrogen atom in an aqueous medium. For example, an ionic polymer that one or more amine or ammonium groups can be referred to as a cationic polymer. In some embodiments, some of the acid or amine groups of an anionic or cationic polymer are derivatized to form esters (e.g., methyl or ethyl esters) or amides (e.g., phthaloyl). Examples of ionic polymers include, but are not limited to, sodium alginate, chitosan, hydroxypropyl chitosan, carrageenan, carboxyalkyl celluloses, such as carboxymethyl cellulose, sodium hyaluronate, mucins, carboxyalkyl chitosan, such as carboxymethyl chitosan, quaternary ammonium chitosan, thiolated quaternary ammonium chitosan, glycidyltrimethylammonium chitosan, diethylaminoethyl chitosan (DEAECs), dimethylaminoethyl chitosan (DMAECs), dimethylaminoisopropyl chitosan (DMAiPCs), and mixtures thereof.

As used herein, "therapeutic agent" refers to a compound that is suitable for administration to humans or other mammals, and can treat a disease, disorder, or condition. In some embodiments, the therapeutic agent is a small-molecule organic compound, e.g., having a molecular weight less than 1 kDa, including, but not limited to, amikacin, ciprofloxacin, streptomycin, rifampicin, isoniazid, ethambutol, pyrazinamide, ibuprofen, tobramycin, epinephrine, salbutamol, salmeterol, clenbuterol, levalbuterol, or a pharmaceutically acceptable salt thereof. In some embodiments, the therapeutic agent is a large-molecule compound, such as an oligopeptide, a polypeptide, an oligonucleotide, a polynucleotide, and the like.

As used herein, "treat" or "treating" or "treatment" can refer to one or more of: delaying the progress of a disease, disorder, or condition; controlling a disease, disorder, or condition; delaying the onset of a disease, disorder, or condition; ameliorating one or more symptoms characteristic of a disease, disorder, or condition; or delaying the recurrence of a disease, disorder, or condition, or characteristic symptoms thereof, depending on the nature of the disease, disorder, or condition and its characteristic symptoms.

As used herein, "administer" or "administering" means to introduce, such as to introduce to a subject a compound or composition. The term is not limited to any specific mode of delivery, and can include, for example, subcutaneous delivery, intravenous delivery, intramuscular delivery, intracisternal delivery, delivery by infusion techniques, transdermal delivery, oral delivery, nasal delivery, ophthalmic delivery, intratracheal delivery, otic delivery, and rectal delivery. Furthermore, depending on the mode of delivery, the administering can be carried out by various individuals, including, for example, a health-care professional (e.g., physician, nurse, etc.), a pharmacist, or the subject (i.e., self-administration). In some embodiments, administering comprises delivering a compound or composition to a subject via insufflation. As used herein, "insufflating" or "insufflation"

refer to administering a solid composition by inhalation, e.g., via the nasal cavity or the mouth.

As used herein, "subject" refers to any mammals such as, but not limited to, humans, horses, cows, sheep, pigs, mice, rats, dogs, cats, and primates such as chimpanzees, gorillas, and rhesus monkeys. In some embodiments, the "subject" is a human. In some embodiments, the "subject" is a human who exhibits one or more symptoms characteristic of a disease, disorder, or condition. In another embodiment, the "subject" is a human who has an infection (e.g., a bacterial infection) of the lower respiratory tract. In some embodiments, such an infection can be a chronic infection, which, for example, may be associated with cystic fibrosis and/or COPD. The term "subject" does not require one to have any particular status with respect to a hospital, clinic, or research facility (e.g., as an admitted patient, a study participant, or the like).

As used herein, the term "in combination with," when used, for example, in the context of administering a compound in combination with another compound, places no limit on the method, mode, form, etc. of the administration, so long as the administration results in both compounds being simultaneously biologically available to a subject at a common point in time.

As used herein, the term "mixture(s) of" or "mixture(s) thereof" refers to any mixture of two or more materials and/or compositions that would be encompassed within the list that follows or precedes the phrase, respectively. The phrase does not refer to any particular type of mixture. Thus, the "mixture" is not necessarily an intimate mixture, a homogeneous mixture, etc. Furthermore, the "mixture" need not contain a representative of each element in the list. For example, if a composition comprises "A, B, C, or a mixture thereof," the term contemplates mixtures of A and B (with no C present), mixtures of B and C (with no A present), mixtures of A and C (with no B present), as well as mixtures of A, B, and C. As a further illustration, suppose that A, B, or C define generic categories (e.g., a chitosan), where, for example, $A^1$ and $A^2$ are species or subgenuses encompassed by the genus A. In that instance, if a composition comprises "A, B, C, or a mixture thereof," the claim also contemplates mixtures of $A^1$ and $A^2$ (where no B and no C are present in the mixture). Of course, when a composition "comprises" such mixtures, other materials can be present as well.

As used herein, the terms "include," "including," "have," "having," "contain," and "containing" possess the same meaning as "comprise" or "comprising," and therefore define an open set. Closed sets shall be defined exclusively by the use of "consisting of" or "consists of."

As used herein, "polysaccharide" refers to branched and unbranched chains of saccharides joined together by glycosidic bonds. These chains can include saccharides that are natural in origin, such as glucose, fructose, galactose, xylose, ribose, and the like, but can also include non-naturally-occurring saccharides. In some embodiments, such saccharides can possess functional groups that are acidic, such as, for example, carboxyl groups, sulfate groups, phosphate groups, and esters thereof. In some embodiments, such saccharide groups can possess functional groups that are basic, such as amines, e.g., glucosamine. Examples of polysaccharides include, but are not limited to, starches, glycogen, celluloses, chitins, such as chitosans, and alginates.

As used herein, the term "hydrogel particle" refers to a particle that contains a water-swellable polymer. The term does not imply that the particle is necessarily in gelatinous state, including absorbed water.

As used herein, "PEGylated" refers to a compound (e.g., a polysaccharide, such as a chitosan or a cellulose) that has at least one polyethylene glycol chain covalently bound to it. The invention is not limited to any particular chain length of the polyethylene glycol or of any particular molecular weight of the PEGylated compound, as long as the resulting PEGylated entity is suitable for formulating into a solid composition suitable for administration by insufflation.

Solid Compositions

In at least one aspect, the invention provides solid compositions for administration of a therapeutic agent. The solid compositions contain an amount of a therapeutic agent. In some embodiments, the solid compositions contain other excipients as well, such as one or more, or two or more, hydrophilic polymers. In some embodiments, the solid composition is sterile, where the composition is made and kept sterile by any suitable means.

The invention is not limited to any particular therapeutic agent. In some embodiments, the therapeutic agent is a small-molecule drug compound, i.e., having a molecular weight of 1000 daltons or less. In other embodiments, the therapeutic agent is a large-molecule drug compound, such as a polypeptide, an oligopeptide, a polynucleotide, or an oligonucleotide. In some embodiments, the therapeutic agent is an antibiotic. In some such embodiments, the therapeutic agent is amikacin, ciprofloxacin, streptomycin, rifampicin, isoniazid, ethambutol, pyrazinamide, ibuprofen, tobramycin, epinephrine, salbutamol, salmeterol, clenbuterol, levalbuterol, or a pharmaceutically acceptable salt thereof. In some embodiments, the therapeutic agent includes a basic group, such as an amine. In some embodiments, the therapeutic agent includes an acidic group, such as a carboxylic acid, a sulfonic acid, or a sulfinic acid. In some embodiments, the therapeutic agent includes both a a basic group and an acidic group. In some further such embodiments, the therapeutic agent is ciprofloxacin or a pharmaceutically acceptable salt thereof. In some embodiments, the pharmaceutically acceptable salt is a salt formed with a counterion that is included in an ionic polymer, such as an anionic polymer or a cationic polymer, or both.

The solid composition may contain any suitable amount of the therapeutic agent. A suitable concentration of the therapeutic agent in the solid composition may be determined by those of skill in the art. Various factors may influence the selection of a suitable concentration, including but not limited to, the identity of the therapeutic agent, the nature of other excipients in the solid composition, and other physical features of the particles in the solid composition. In some embodiments, the solid composition contains from 50 to 1000 mg/mL, or from 100 to 750 mg/mL, or from 125 to 500 mg/mL of the therapeutic agent. In some embodiments, the solid composition contains about 125 mg/mL, or 250 mg/mL, or 375 mg/mL, or 500 mg/mL of the therapeutic agent.

The solid composition comprises a plurality of hydrogel particles. In some embodiments, the hydrogel particles include one or more water-swellable polymers. Such polymers can be PEGylated or non-PEGylated. In some embodiments, one or more of these polymers can be a hydrophilic polymer. In some such embodiments, one or more of these polymers can be an ionic polymer. The invention is not limited to hydrogel particles having any particular amount of water-swellable polymer. In some embodiments, the water-swellable polymer is at least 40% by weight, or at least 50% by weight, or at least 60% by weight, or at least 70% by weight, or at least 80% by weight, or at least 90% of the hydrogel particles, based on the total weight of dry ingredients in the hydrogel particle.

The invention is not limited to any particular size of hydrogel particle. Different sizes of particles can be used for different applications, such as different modes of delivery. In some embodiments, the hydrogel particles have a size that is suitable for intratracheal administration, e.g., by insufflation. In some embodiments, the hydrogel particles have a mass median aerodynamic diameter of 0.5 to 5.0 µm, or 1.0 to 4.0 µm. In some embodiments, the mass median aerodynamic diameter of the hydrogel particles is about 1.0 µm, or 1.5 µm, or 2.0 µm, or 2.5 µm, or 3.0 µm, or 3.5 µm, or 4.0 µm. In other embodiments, the mean particle size of a hydrogel particle is from 150 to 300 nm, or from 175 to 250 nm, as measured by dynamic light scattering. In some embodiments, the volume mean diameter of the hydrogel particles is 2.0 to 5.0 µm, or 2.5 to 4.5 µm, or 3.0 to 4.0 µm, as measured by laser diffraction.

In some embodiments, the solid composition comprising the hydrogel particles can be defined by certain physical properties, such as a tapped density. The invention is not limited to solid compositions having any particular tapped density, as long as the solid composition is suitable for intratracheal administration, e.g., by insufflation. In some embodiments, the solid composition has a tapped density of 0.25 to 0.50 g/mL, or 0.30 to 0.45 g/mL.

In some embodiments of the invention, the hydrogel particles contain one or more hydrophilic polymers. In some such embodiments of the invention, the hydrogel particles contain one or more ionic polymers. In some such embodiments, the hydrogel particles contain two or more ionic polymers. The invention is not limited to any particular hydrophilic or ionic polymers. In some embodiments, the two or more ionic polymers include an alginate, a chitin, such as a chitosan, a cellulose, such as a hydroxylated cellulose or a carboxylated cellulose, a mucin, a carrageenan, a hyaluronate, and the like, or any PEGylated derivatives of the foregoing, or any mixtures thereof. In some embodiments, at least one of the two or more ionic polymers is an anionic polymer, such as an alginate, a carrageenate, a hyaluronate, or a polysaccharide that includes an anionic group, such as a carboxylate, a sulfonate, a sulfate, a phosphonate, phosphinate, or a phosphate. In some embodiments, one or more of the one or more ionic polymers is PEGylated. In some embodiments, at least one of the two or more anionic polymers is a cationic polymer, such as a polysaccharide that includes amine groups, e.g., a chitosan or an aminated cellulose. In some embodiments, one or more of the one or more cationic polymers is PEGylated. In some embodiments, the solid composition consists essentially of a therapeutic agent (according to any of the above embodiments) and one or more, or two or more, ionic polymers (according to any of the above embodiments).

In some embodiments, the hydrogel particles contain one or more PEGylated hydrophilic polymers and one or more non-PEGylated hydrophilic polymers. In some embodiments, the hydrogel particles contain one or more PEGylated ionic polymers and one or more non-PEGylated ionic polymers. The invention is not limited to any particular ratio of PEGylated polymers to non-PEGylated polymers. In some embodiments the weight/weight ratio of PEGylated polymers to non-PEGylated polymers in a hydrogel particle ranges from 10:1 to 1:10, or from 5:1 to 1:5, or from 3:1 to 1:3. In some embodiments, the weight/weight ratio of PEGylated ionic polymers to non-PEGylated ionic polymers in a hydrogel particle is about 1:5, or 1:4, or 1:3, or 1:2, or 1:1, or 2:1, or 3:1, or 4:1, or 5:1.

In some embodiments of the invention, the solid composition comprises excipients (e.g., ingredients in the solid composition besides the therapeutic agent) that are biodegradable within the environment of the lungs and lower respiratory tract. In this context, "biodegradable" refers to materials that, within the environment of the lungs and/or lower respiratory tract, that do not accumulate within the lung after repeated administrations of the solid composition by insufflation under normal dosing conditions. In some embodiments, less than 2% by weight, or less than 1.5% by weight, or less than 1% by weight, or less than 0.5% by weight, of the excipients in the solid composition are not biodegradable within the environment of the lungs and/or lower respiratory tract, based on the total dry weight of excipients in the solid composition.

In some embodiments, the hydrogel particles are adapted to swell when exposed to an aqueous medium or an aqueous environment, such as the environment in the lungs and the lower respiratory tract. In some embodiments, this swelling can occur within 30 minutes, or 20 minutes, or 15 minutes following intratracheal administration to a subject (e.g., a human subject) by insufflation. In some such embodiments, the hydrogel particles increase their volume mean diameter by at least 2 times, or at least 4 times, or at least 6 times, or at least 8 times, or at least 10 times, following intratracheal administration to a subject (e.g., a human subject) by insufflation (e.g., within 15 minutes, or 20 minutes, or 30 minutes).

In some embodiments, the solid composition can contain other excipients, such as various fillers and binders. Such components are well known in the art. In some embodiments, the solid composition can include amounts of one or more pharmaceutically acceptable sugars, including, but not limited to, fructose, galactose, glucose, lactitol, lactose, maltitol, maltose, mannitol, melezitose, myoinositol, palatinite, raffinose, stachyose, sucrose, trehalose, xylitol, and any hydrates thereof. Various other excipients are included in REMINGTON: THE SCIENCE AND PRACTICE OF PHARMACY, 21ST EDITION, (Mack Publishing, 2005).

Process for Forming Solid Composition

In at least another aspect, the invention provides methods for making the solid compositions described above. Insofar as the solid composition is concerned, the invention is not limited to any particular method of forming the composition or the hydrogel particles. In some embodiments, however, the solid composition is a powder. In some such embodiments, the powder is formed by spray drying, where the solid ingredients are dissolved and/or suspended in a liquid medium (e.g., an aqueous medium, such as a gel) and are sprayed into a drying chamber in a manner that allows the liquid medium to evaporate, leaving behind an evaporation residue. In some other embodiments, the powder containing the hydrogel particles is formed by spray granulation. In some other embodiments, the powder containing the hydrogel particles is formed by freeze drying. In some other embodiments, the powder containing the hydrogel particles is formed by spray gelation.

In embodiments that employ spray drying, the invention is not limited to any particular method of performing the spray drying. Those of skill in the art are well acquainted with methods of obtaining pharmaceutical powders through the use of spray drying. Any suitable solvent can be used as the liquid medium. Acceptable solvents include, but are not limited to, water or other polar solvents such as alcohols, for example ethanol and isopropanol, ketones, for example acetone, and mixtures thereof. In various embodiments, the solvent may be chosen from water, ethanol, and acetone. In some embodiments, the solid materials added to the solution or suspension can be treated, e.g., by milling, homogenization, etc. The sprayed solution or suspension may also include various wetting agents, such as Pluronic. In some embodiments, the solution or suspension can be filtered prior to spraying, so as to remove clumps or other particles that may clog the sprayer.

Removal of the solvent from the solution or suspension may, in some embodiments, comprise spray drying the solution or suspension to form a powder. In some other embodiments, the solution may be sprayed onto a solid pharmaceutically acceptable carrier. As used herein, "solid pharmaceutically acceptable carrier" refers to any suitable solid excipient. Suitable carriers include, but are not limited to, polysaccharides, for example, starches, lactose, sucrose, glucose, and mannitol, silicic acid, calcium carbonate, calcium phosphate, sodium phosphate, crospovidone, and kaolin. In some embodiments, a carrier can include one or more ionic polymers (according to the embodiments described above). In some embodiments, the carrier can also include an amount of a therapeutic agent. In other embodiments, the therapeutic agent is included in the sprayed solution or suspension.

Dosage Forms

The invention is not limited to any particular dosage form. The invention includes, for example, dosage forms that are suitable for administration by a variety of means, such as subcutaneous delivery, intravenous delivery, intramuscular delivery, intracisternal delivery, delivery by infusion techniques, transdermal delivery, oral delivery, nasal delivery, ophthalmic delivery, intratracheal delivery, otic delivery, and rectal delivery. The design of dosage forms suitable for such modes of delivery is well known in the art. See, for example, REMINGTON: THE SCIENCE AND PRACTICE OF PHARMACY, 21ST EDITION, (Mack Publishing, 2005). In some embodiments, solid compositions of the invention can be incorporated into dosage forms suitable for oral delivery, such as tablets, capsules, powders, suspensions, and the like. In other embodiments, solid compositions of the invention can be incorporated into solutions or suspensions for intravenous delivery. In other embodiments, solid compositions of the invention can be incorporated into solutions or suspensions for ophthalmic delivery. In some other embodiments, solid compositions of the invention can be incorporated into solutions, suspensions, or powders for nasal, otic, or intratracheal delivery.

In some embodiments, the solid composition can be administered to a subject intratracheally. Thus, in such embodiments, the solid composition can be packaged in a dosage form that is suitable for intratracheal administration to a human subject, e.g., by insufflation. In some embodiments, such dosage forms comprise an aerosol formulation, where a dry powder is administered directly to the trachea using a device, such as a powder insufflator or an inhaler, that can generate an aerosol containing a solid composition (of any of the above embodiments).

In such embodiments, one may use any suitable means of generating a powder aerosol. Aerosol devices for intratracheal delivery are well known in the art. For example, Penn-Century, Inc. (Wyndmoor, Pa.) supplies an insufflator, Model DP-4, that is suitable for delivery of a dry powder. Such insufflators do not make use of a propellant.

In other embodiments, one can use an inhaler that makes use of a propellant. In such embodiments, the solid composition further includes a propellant. In some embodiments, the propellant is a compressed gas, such as air, nitrogen, nitrous oxide, $CO_2$, or mixtures thereof, or a liquefied gas, or a mixture of liquefied gases. Any propellant used in the art of preparing aerosol formulations may be used. In some other embodiments, however, a chemical propellant is used. Chemical propellants are well known in the art; any suitable chemical propellant will suffice. In some embodiments, the chemical propellant is a halogenated hydrocarbon, such as a chlorofluorocarbon, a hydrochlorofluorocarbon, a hydrogen-containing fluorocarbon, a perfluorocarbon, a hydrocarbon, or any mixtures thereof. In some embodiments, the propellant is a hydrochlorofluorocarbon, a hydrogen-containing fluorocarbon, a perfluorocarbon, or a mixture thereof. In some embodiments, the propellant includes a chlorofluorocarbon, such as one or more of dichlorotetrafluoroethane (e.g., $CClF_2CClF_2$, $CCl_2FCF_3$), trichlorofluoromethane, dichlorodifluoromethane, chloropentafluoroethane, or mixtures thereof. In some embodiments, the propellant includes a hydrochlorofluorocarbon, such as chlorodifluoromethane, chlorodifluoroethane (e.g., 1-chloro-1,1-difluoroethane), or mixtures thereof. In some embodiments, the propellant includes a hydrogen-containing fluorocarbon, such as $CHF_2CHF_2$, 1,1,1,2-tetrafluoroethane, difluoroethane (e.g., 1,1-difluoroethane), 1,1,1,2,3,3,3-heptafluoro-propane, or mixtures thereof. In some embodiments, the propellant includes a perfluorocarbon, such as hexofluoroethane, octafluoropropane, octafluorocyclobutane, or mixtures thereof. In some embodiments, the propellant includes a hydrocarbon, such as propane, isobutane, n-butane, dimethyl ether, or mixtures thereof. In some embodiments, the propellant comprises one or more of difluoroethane, $CHF_2CHF_2$, 1,1,1,2-tetrafluoroethane, 1,1,1,2,3,3,3-heptafluoropropane, hexafluoroethane, octafluoropropane, octafluorocyclobutane, or mixtures thereof.

In embodiments that employ an aerosol formulation, the aerosol formulation may be prepared by any suitable means known in the art. In some embodiments, the aerosol formulation is prepared by employing a cold filling process, whereby initially the components of the aerosol formulation and an aerosol container are cooled, e.g., to about −40° C., such that the propellant liquefies to some degree. All components except for the propellant are placed into the aerosol container. Thereafter, the carrier is added, the components mixed, and a valve assembly inserted into place. The valve assembly is then crimped such that the container is airtight. Thereafter, the container and formulation contained therein are allowed to return to ambient temperature. In some other embodiments, other processes can be used. For example, in some other embodiments, an aerosol formulation may be prepared by transfer of a propellant from a bulk container. In such a process, the components except for the propellant are initially placed into an empty aerosol container. A valve assembly is then inserted and crimped into place. The propellant, under pressure and in liquid form, is metered through the valve assembly from a bulk container or tank of carrier. The container housing the formulation is checked to ensure that the pressurized contents do not leak. In other embodiments, other suitable means of preparing aerosol formulations are carried out.

Methods of Treatment

In another aspect, the invention provides methods of treating a lower respiratory tract infection. In some embodiments, the methods comprise intratracheally administering to a subject an effective amount of a solid composition, where the solid composition comprises a plurality of hydrogel particles (according to any of the above embodiments) that contain a therapeutic agent. In some embodiments, the methods comprise insufflating a subject (e.g., administering via inhalation) an effective amount of a solid composition, where the solid composition comprises a plurality of hydrogel particles (according to any of the above embodiments) that contain a therapeutic agent.

In some embodiments, the therapeutic agent is an antibacterial agent. In some such embodiments, the antibacterial agent is amikacin, ciprofloxacin, streptomycin, rifampicin, isoniazid, ethambutol, pyrazinamide, ibuprofen, tobramycin, epinephrine, salbutamol, salmeterol, clenbuterol, levalbuterol, or a pharmaceutically acceptable salt thereof. In some embodiments, the antibacterial agent is ciprofloxacin or a pharmaceutically acceptable salt thereof. The dosed amount will vary depending on a number of factors, including, but not limited to, characteristics of the subject (weight, health, age, etc.), the nature of the condition being treated, and the identity of the therapeutic agent. In some embodiments, a single dose of the solid composition includes delivery of 100 to 2000 mg, or from 200 to 1500 mg, or from 250 to 1000 mg of the therapeutic agent. In some embodiments, a single dose of the solid composition includes delivery of about 250 mg, or about 500 mg, or about 750 mg, or about 1000 mg of the therapeutic agent. In some embodiments, dosing can be done at such levels from once to three times daily. In some embodiments, dosing at such levels is done once a day, or twice a day, or three times a day. The treatment can be continued as long as necessary.

In some embodiments, the administration is carried out to treat a respiratory tract infection, such as a lower respiratory tract infection. In some embodiments, the lower respiratory tract infection is an acute infection, such as pneumonia or bronchitis. In some other embodiments, the respiratory tract infection is a chronic infection, which, for example, can be associated with conditions such as asthma, cystic fibrosis, or chronic obstructive pulmonary disease (COPD).

The administration of the therapeutic agent can be carried out in combination the administration of other therapeutic agents. For example, the therapeutic agents can be administered in combination with aminoglycoside antibiotics, such as gentamicin, ataluren, fosfomycin, ivacaftor, various bronchodilators, such as $\beta_2$ agonists and anticholinergics, corticosteroids, phosphodiesterase inhibitors, such as roflumilast and cilomilast, and various tumor necrosis factor antagonists, such as infliximab.

EXAMPLES

The following examples illustrate various embodiments of the invention. No example is intended to limit the scope of the invention, but is rather intended to show embodiments thereof.

Example 1—Synthesis of PEG Grafted onto Phthaloyl Chitosan (PHCs)

The synthesis of polyethylene glycol (PEG) grafted onto PHCs is modified based on a synthesis described in the literature in the following references, each of which is incorporated herein by reference in its entirety: El-Sherbiny & Smyth, Int'l J. Pharm., Vol. 395(1-2), pp. 132-141 (August 2010); and El-Sherbiny & Smyth, J. Microencapsul., Vol. 27(8), pp. 657-668 (2010).

PHCs was synthesized by reaction of 5 g of Cs (chitosan) with 22.5 g of phthalic anhydride in 150 mL of dimethylformamide (DMF) at 130° C. under dry nitrogen atmosphere for 10 hours. The reaction mixture was left to reach room temperature and then the PHCs was precipitated over ice-water. The precipitated PHCs was filtered, washed with ethanol, and freeze dried. Then, m-PEG was converted into m-PEG-COOH through reaction with succinic anhydride. In brief, 10 g of m-PEG, 0.24 g of DMAP, 0.24 g of succinic anhydride, and 0.2 g of triethylamine were dissolved in 50 mL of dry dioxane. The reaction mixture was stirred at room temperature for 2 days under inert atmosphere. The dioxane was evaporated and the residue (m-PEG-COOH) was taken up in $CCl_4$, filtered and precipitated by diethyl ether. The PEG-g-PHCs copolymer was obtained by stirring of 3.8 g of m-PEG-COOH with 0.5 g of the dried PHCs in 15 mL DMF. Then, 0.3 g of the t-butyl alcohol (HOBt) was added and the reaction mixture was stirred at room temperature until obtaining a clear solution. Afterwards, 1-ethyl-3-(3-dimethyl-aminopropyl)carbodiimide hydrochloride (EDC.HCl) (0.43 g) was added and the reaction was continued overnight under stirring at room temperature. The obtained PEG-g-PHCs copolymer was purified by dialysis in distilled water, washed with ethanol and freeze dried.

Example 2—Preparation of Hydrogel Particles

Ciprofloxacin (CF)-loaded hydrogel particles were obtained via spray drying of a combination of CF-loaded PEG-g-PHCs nanoparticles suspension and sodium alginate solution. Briefly, homogenous solutions of the CF-loaded PEG-g-PHCs nanoparticles (1% w/v) and sodium alginate (3% w/v) were prepared using 0.06% acetic acid and distilled water as solvents, respectively. The self-assembled PEG-g-PHCs nanoparticles were prepared by sonication of 1% w/v copolymer solution containing CF using a probe type sonicator (Misonix ultrasonic processor, S-4000, Misonix Inc., Farmingdale, N.Y.) at 60 W for 2 min. The sonication step was repeated twice and performed in an ice-water bath. Then, a 75 mL of CF-loaded PEG-g-PHCs nanoparticles suspension was added dropwise with stirring to 25 mL of 3% aqueous alginate solution. The mixture was completed with distilled water up to a final concentration of 1.5% w/v. Then, the homogenized polymer mixture was spray-dried with a 0.7 mm two-fluid pressurized atomizer at a feed rate of 25% (6 mL/min) in a Büchi Mini spray dryer B-290 (Büchi Labortechnik A G, Flawil, C H). The atomizing air flow rate was 500-600 NL/h. The inlet temperature was adjusted at 125° C. and the outlet temperature was varying between 60 and 65° C. The obtained hydrogel particles powder was collected and the spray drying yield (%) was calculated.

Example 3—Determination of Particle Size

The size of the ciprofloxacin-loaded PEG-g-PHCs nanoparticles was estimated using dynamic light scattering (Wyatt Technology Corporation Dyna Pro-titan DLS) after sonication of a 1% PEG-g-PHCs solution for 2 min at a power of 60 watt. Size of the hydrogel microparticles was determined using laser diffraction (SYMPATEC, Sympatec Gmbt, System Partikl-Technik, Germany with a He—Ne laser beam 5 mW max at 632.8 nm). The measurements were carried out in triplicates for the suspension of the microparticles in acetone. Volume mean diameter (VMD, μm) was calculated from the particle size distribution curves for the microparticles. Average aerodynamic diameter of the CF-loaded microparticles was also calculated using the following relationship:

$$d_a = d_g(\rho_p/\rho_0\chi)^{0.5}$$

where, $d_a$ is the microparticles aerodynamic diameter (μm), $d_g$ is the geometric diameter (VMD, μm), $\rho_p$ is the microparticles tapped density (g/cc), $\rho_0$ is the standard density (1 g/cc) and $\chi$ is the dynamic shape factor.

The size of the prepared ciprofloxacin-loaded nanoparticles was found to be 218.6±25.3 nm as determined by DLS. In the case of the prepared hydrogel microparticles, the volume mean diameters, VMDs of plain and CF-loaded microparticles were determined using laser diffraction and were found to be 2.13±0.04, and 3.87±0.09 μm, respectively. The developed hydrogel nano-microparticles showed relatively low tapped densities (0.298 and 0.347 g/mL for plain and CF-loaded particles, respectively). The aerodynamic diameters ($d_a$) of both CF-free and CF-loaded particles were also determined with the aid of particle densities and found to be 1.16±0.7 and 2.28±0.1 μm.

Example 4—Morphology of Hydrogel Particles

The morphology of the prepared ciprofloxacin-loaded swellable microparticles was examined by SEM (Hitachi S-800 field emission scanning electron microscope operated in secondary electron mode with a Robinson backscatter detector and with a Hitachi PCI system for digital image capture). Dry particles were mounted on aluminum stubs with double-sided conducting carbon tapes and coated with a 50/50 mixture of Au/Pd to minimize surface charging. The samples were scanned at an accelerating voltage of 20 KV.

FIG. 1 shows the scanning electron micrographs of the developed hydrogel microparticles encapsulating ciprofloxacin-free and CF-loaded PEG-g-PHCs nanoparticles. As apparent from the figure, the prepared hydrogel particles have, in general, a spherical nature with relatively smooth and integrated surfaces in the case of CF-free particles (FIG. 1a). These smooth surfaces have turned to show rough surfaces upon incorporating CF-loaded nanoparticles in the alginate matrices (FIG. 1b). The surface roughness may be attributed to the rapid crosslinking process between the positively charged suspension of the CF-loaded PEG-g-PHCs nanoparticles and the negatively charged sodium alginate chains during the spray drying process.

Example 5—Dynamic Swelling Study

The swelling pattern of the developed ciprofloxacin-loaded swellable particles in phosphate buffered saline (PBS), pH 7.4 was studied by determining the increase in both VMD (μm) and the median diameter ($X_{50}$, μm) of the particles with time using laser diffractometer (SYMPATEC, Sympatec Gmbt, System Partikl-Technik, Germany).

Figure 2:
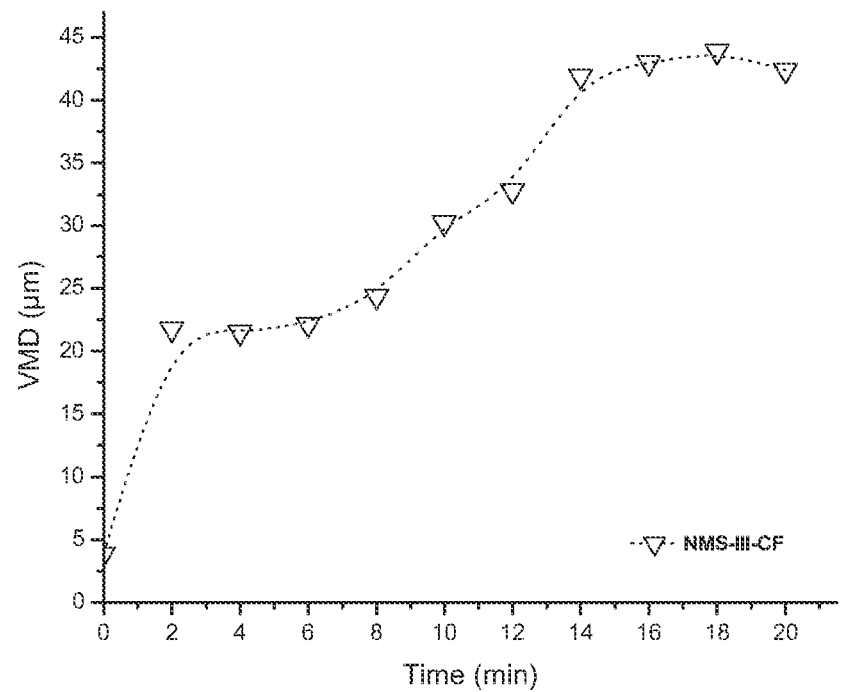
FIG. 2 shows the dynamic swelling pattern of ciprofloxacin-loaded hydrogel particles in PBS at pH=7.4.

The swelling profile of the hydrogel microparticles incorporating ciprofloxacin-loaded PEG-g-PHCs self-assembled nanoparticles in PBS, pH 7.4 is shown in FIG. 2. As apparent from the figure, the swelling profile of the developed hydrogel particles was obtained through determining the increase in the volume mean diameter (VMD, μm) of the particles at various time intervals using laser diffraction technique. As shown in FIG. 2, the prepared hydrogel particles showed a fast initial swelling within the first few minutes. For instance, the VMD of the developed particles has increased from about 3 μm when dry to 22 μm after 2 min of swelling. This swelling continues regularly with time to reach 41.9 μm at 14 min. The swelling can be attributed to the hydrophilic nature of the PEG side chains in the PEG-g-PHCs copolymer and the sodium alginate. As the swelling behavior demonstrates, the developed microparticles which have respirable aerodynamic sizes when dry, showed large geometric sizes when swollen after short time in simulated moist environment of the lungs. This behavior enables the CF delivery systems to avoid macrophage uptake and at the same time confer sustained release of the CF through a controlled polymeric architecture.

Example 6—In Vitro Release Study

The in vitro release pattern of the ciprofloxacin from the developed ciprofloxacin-loaded carrier particles was determined by transferring a certain weight (10-30 mg) of particles to a vial containing 1.5 ml of PBS, pH 7.4. Samples were maintained at 37° C. with shaking at 100 rpm. At predetermined intervals, 100 μL aliquot was withdrawn and analyzed at $\lambda_{max}$ 280 nm using a UV-Vis spectrophotometry. The withdrawn aliquots were replaced with the same volume of fresh buffer, to keep the volume of the release medium constant. The amounts of ciprofloxacin released (μg) from the swellable particles were then calculated using a standard curve of ciprofloxacin in PBS, pH 7.4. Results were expressed as cumulative release (%) relative to the initially loaded weight of ciprofloxacin in the particles. The data points represent average ±SD from three independent experiments.

Figure 3:
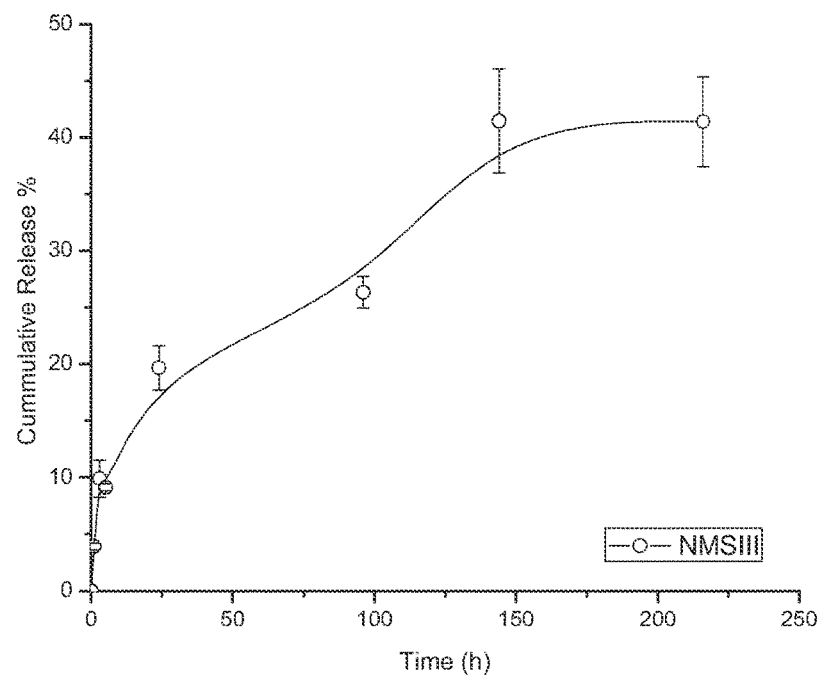
FIG. 3 shows the in vitro cumulative release of ciprofloxacin from a ciprofloxacin-loaded hydrogel particle.

The entrapment efficiency of ciprofloxacin in the developed swellable particles as quantified using UV-Vis spectrophotometry was found to be 30%. The in vitro release profile of CF from the developed swellable particles is illustrated in FIG. 3. As apparent from the figure, the investigated formulation showed a fast initial release of CF (about 9%) within the first 5 hours followed by a relatively slow release up to 144 hours.

Example 7—Cytotoxicity Assay

The effect of the developed ciprofloxacin-loaded swellable particles on the viability of RAW 264.7 cells was investigated. Cells were seeded in 96-well plates at 50,000 cells/well and incubated for 24 h at 37° C. and 5% $CO_2$. Fifty microliters of particles suspension (320, 800 and 1600 μg/mL) were incubated with cells for 24 h. Control cells were grown without adding swellable particles. The cell viability was estimated using a MTT cell proliferation assay kit provided by ATCC (Manassass, Va.). After addition of the MTT reagent (10 μL), the cells were incubated at 37° C. and 5% $CO_2$ for 4 hours until the purple precipitate was visible. Afterwards, 100 μL of detergent reagent was added and the cells were left in the dark at room temperature for 2 hours. Cell viability was determined through recording absorbance at 570 nm. Data represents average absorbance of triplicate samples ±SD.

Figure 4:
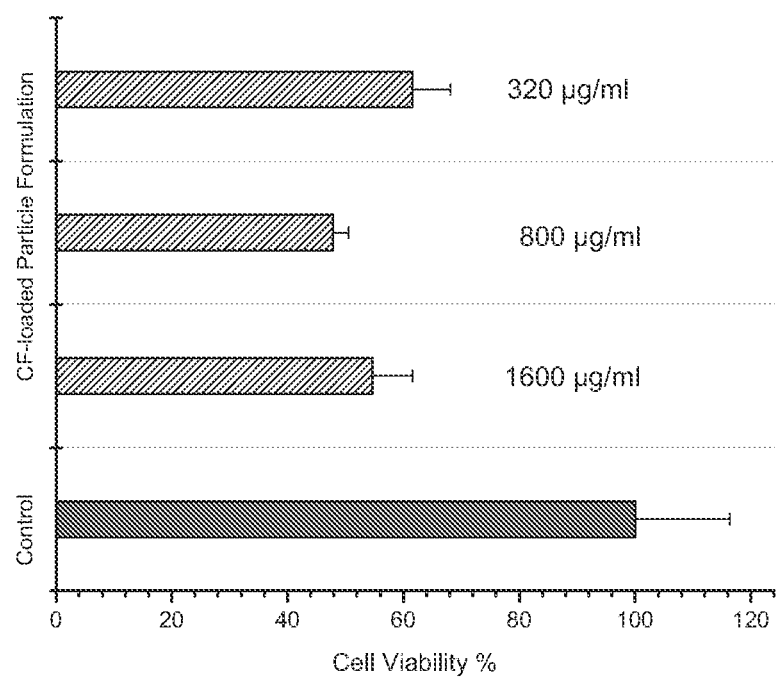
FIG. 4 shows the effect of different concentrations (320, 800, and 1600 mg/mL) of ciprofloxacin-loaded swellable particles on the viability of RAW 264.7 macrophage cells. Cells were seeded at 50,000 cells per well and incubated with particles for 24 hours at 37° C. and 5% $CO_2$.

The viability of the Raw 264.7 cells was determined after the exposure of the cells for 24 h to CF-loaded swellable microparticles at different concentrations as apparent in FIG. 4. From the figure, at the concentration of 320 μg/mL of the CF-loaded microparticles, the viability of the Raw 264.7 cells has been reduced by 38.4% as compared to the control cells under the same experimental conditions. This reduction in the cell viability may be attributed to the CF. The effect of particle concentration (320, 800, and 1600 μg/ml) onto the cells viability was also estimated using the MTT assay. From the figure, within the investigated range of concentrations, there is no significant statistical differences ($p > 0.05$) in the viability of the cells incubated with the three different concentrations. The obtained results tend to show a relatively low cytotoxic potential for the developed swellable drug delivery carrier particles.

Example 8—In Vivo Studies

Male Sprague-Dawley (SD) rats weighing 350±30 g were obtained from the Charles River, and maintained for 12 h light, 12 h dark cycle. Rats were acclimated for 3 days before the experiment and were allowed free access to standard food and water. Temperature and relative humidity were maintained at 25° C. and 50%, respectively. All animal procedures were approved by the Institutional Animal Care and Use Committee (IACUC) of the Univ. of Texas at Austin.

Male SD rats were randomly assigned to 2 groups, receiving formulation as follows: Group 1, the mixture of ciprofloxacin with Lactose (ciprofloxacin concentration: 30% w/w); Group 2, ciprofloxacin-loaded swellable particle (ciprofloxacin concentration: 30% w/w). The dosage of ciprofloxacin was 15 mg/kg.

Briefly, prior to dosing, all rats were anesthetized by IP injection of ketamine (75 mg/kg)/xylazine (5 mg/kg) cocktail. The footpads were pinched firmly to test for the lack of pedal reflex. The powder formulations were administered as described here. Each animal was placed flat on its abdomen and the trachea visualized with the help of a laryngoscope. A small animal insufflator (Penn-Century DP-4, Penn Century, Philadelphia, Pa.) was inserted into the trachea and placed at a distance of 1 cm from the carina. The powder (4.5 mg per time, total 4 times) in the chamber of insufflator was dispersed with the help of 2 mL of air from an empty syringe. After insufflation, each animal was held in an upright position for 1 minute to ensure appropriate deposition of powder in the lung, then maintained at 30° C. during the recovering period on the heating pad. The insufflator containing the powder was weighed before, after powder filling, and after administration, to know the exact dose insufflated.

For sampling after administration, a 0.4 mL blood sample was collected from the jugular vein. As for the lavage collection, animals were euthanized via $CO_2$ inhalation and exsanguinated. The trachea were severed below the glottis between the thyroid glands, and the right main bronchus were clamped and tied off to isolate the right lobe for whole tissue analysis. The trachea was immediately cannulated and the lungs were lavaged three times with 1 mL buffer of acetic acid/sodium acetate buffer, pH 3.4 (obtained by mixing 5 volumes of 0.1 M sodium acetate with 95 volumes of 0.1 M acetic acid). The collected lavage was put in a 2 mL tube and kept in ice until analysis. Following lavage collection, the right lobe was removed for homogenization. The isolated right lobe was retrieved intact, weighed and placed into a 50 mL conical tube, snap frozen and stored at −80° C. until homogenization. For homogenization, lung tissues were thawed and 2 mL of lavage buffer was added to each 50 mL tube. Lungs were homogenized and the subsequent tissue slurry was analyzed for drug content.

The concentration of the ciprofloxacin in the plasma, lavage and lung tissue, were measured by using a high performance liquid chromatography (HPLC) system with an UV detector at room temperature. An aliquot of samples was injected onto an HPLC column (Atlantis T3 Column, 4.6× 250 mm, 5 μm, Waters Corporation, MA, USA). The mobile phase consisted of a mixture of 800 mL of 50 mL/L acetic acid, 110 mL of acetonitrile, and 90 mL of methanol per liter. The UV detector was set at 280 nm. The flow rate was 1 mL/min.

The obtained data was analyzed and expressed as mean±SD. Effects of various parameters were statistically analyzed by one-way ANOVA. Differences were considered significant at the level of $p<0.05$.

Figure 5:
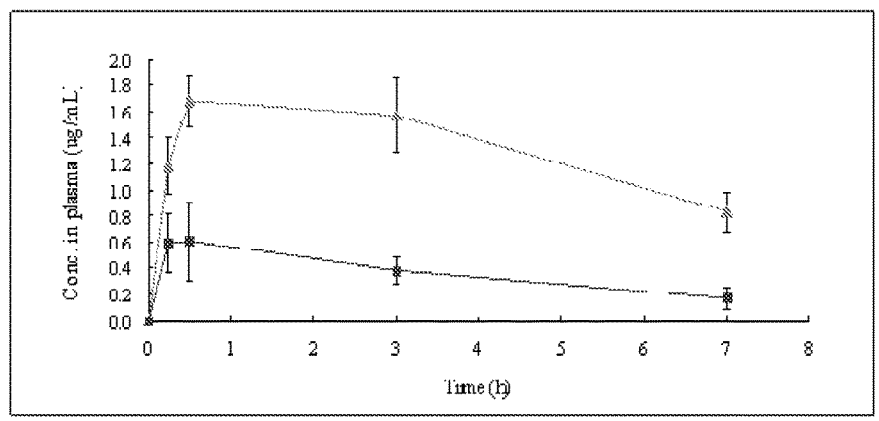
FIG. 5 shows the concentration of ciprofloxacin in plasma for the ciprofloxacin-loaded hydrogel particles (upper curve), and the ciprofloxacin in plasma for a mixture of ciprofloxacin and lactose (lower curve). The dosage of ciprofloxacin was 15 mg/kg.
Figure 6:
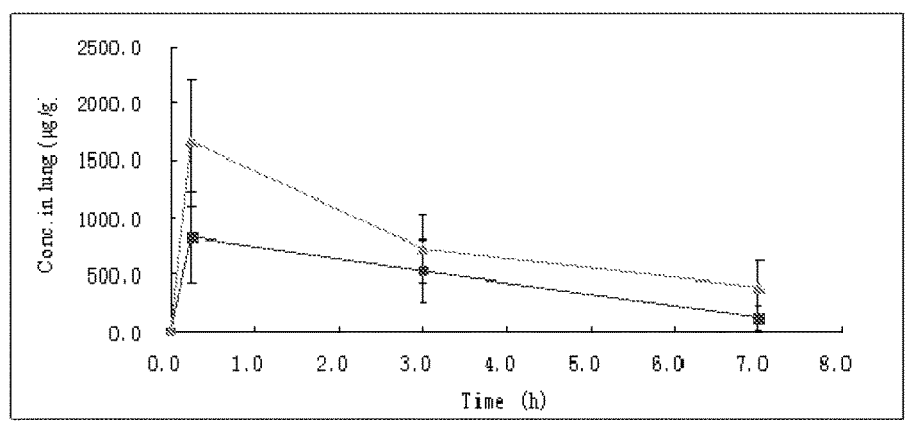
FIG. 6 shows the concentration of ciprofloxacin in rat lung tissue for the ciprofloxacin-loaded hydrogel particles (upper curve), and the ciprofloxacin in rat lung tissue for a mixture of ciprofloxacin and lactose (lower curve). The dosage of ciprofloxacin was 15 mg/kg.
Figure 7:
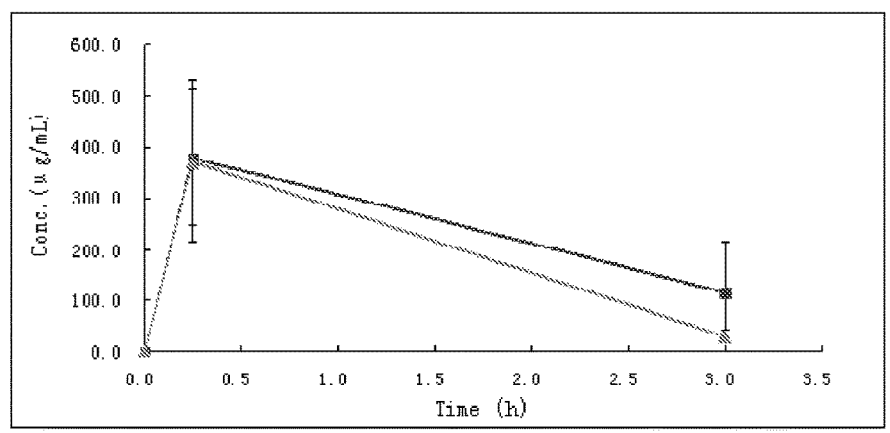
FIG. 7 shows the concentration of ciprofloxacin in lavage for the ciprofloxacin-loaded hydrogel particles (lower curve), and the ciprofloxacin in lavage for a mixture of ciprofloxacin and lactose (upper curve). The dosage of ciprofloxacin was 15 mg/kg.
Figure 8:
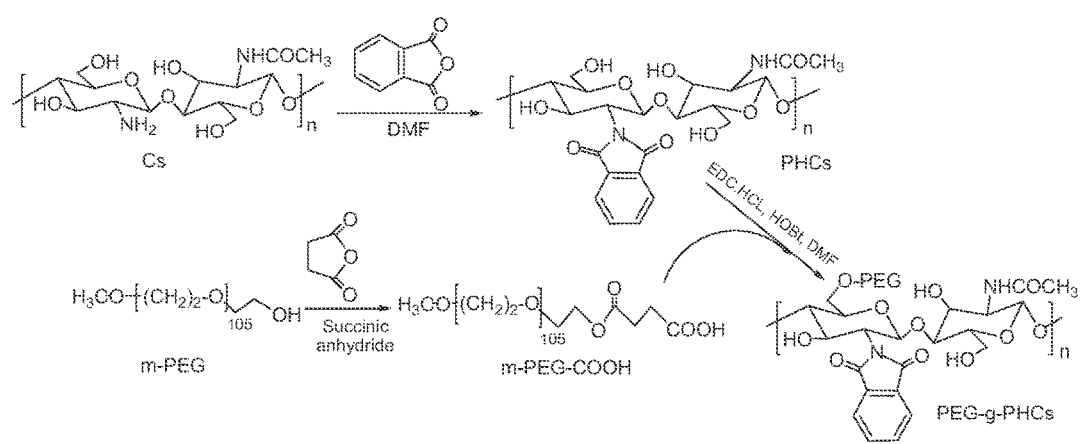
FIG. 8 shows a schematic for the synthesis of PEGylated phthaloyl chitosan copolymer.

Plots of average ciprofloxacin plasma concentration versus time after administration of two dry powder formulations to SD rats are shown in FIG. 5. As apparent from the figure, there is a statistical difference in concentrations between swellable particle formulation and the mixture powder formulation at all time points ($p<0.05$). The pharmacokinetic parameters were calculated by non-compartmental methods (Sung et al., *Pharm. Res.* Vol. 26(8), pp. 1847-55 (2009)). For plasma, the areas under the curve ($AUC_{0-7h}$) are 11.608 μg*h/mL, and 2.802 μg*h/mL for the group of swellable particles and the mixture powder group, respectively. Ciprofloxacin concentration in the lung tissue was also estimated and found to be higher in the case of swellable particles group than that in the mixture group at 0.25 h and 3.0 h, as can be noted from FIG. 6. From the figure, the concentration of the drug released from the swellable particles decreased by almost 50% within the first three hours. In lavage (FIG. 7), ciprofloxacin concentration did not demonstrate significant differences between the two groups at the various time points.

Although there was a sharp increase of ciprofloxacin concentration in plasma within 0.3 hours (FIGS. 5 and 6), the swellable particles formulations led to a relatively prolonged ciprofloxacin presence in the plasma and lungs up to 7 hours after administration. Also, as can be noted from FIG. 5, swellable particles showed higher ciprofloxacin levels in the plasma than the mixture formulation, providing evidence for a delayed release from the swellable particles. The higher concentration in the lungs may be attributed to at least two factors. The swellable particle formulation could extend the adhesion time between particles and lung epithelial cells, and/or the excipients in the particle could trigger uptake of the particle by lung cells.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the agent" includes reference to one or more agents and equivalents thereof known to those skilled in the art, and so forth.

Example 9A—G-Block (Oligoguluronate) Extraction

Figure 9:
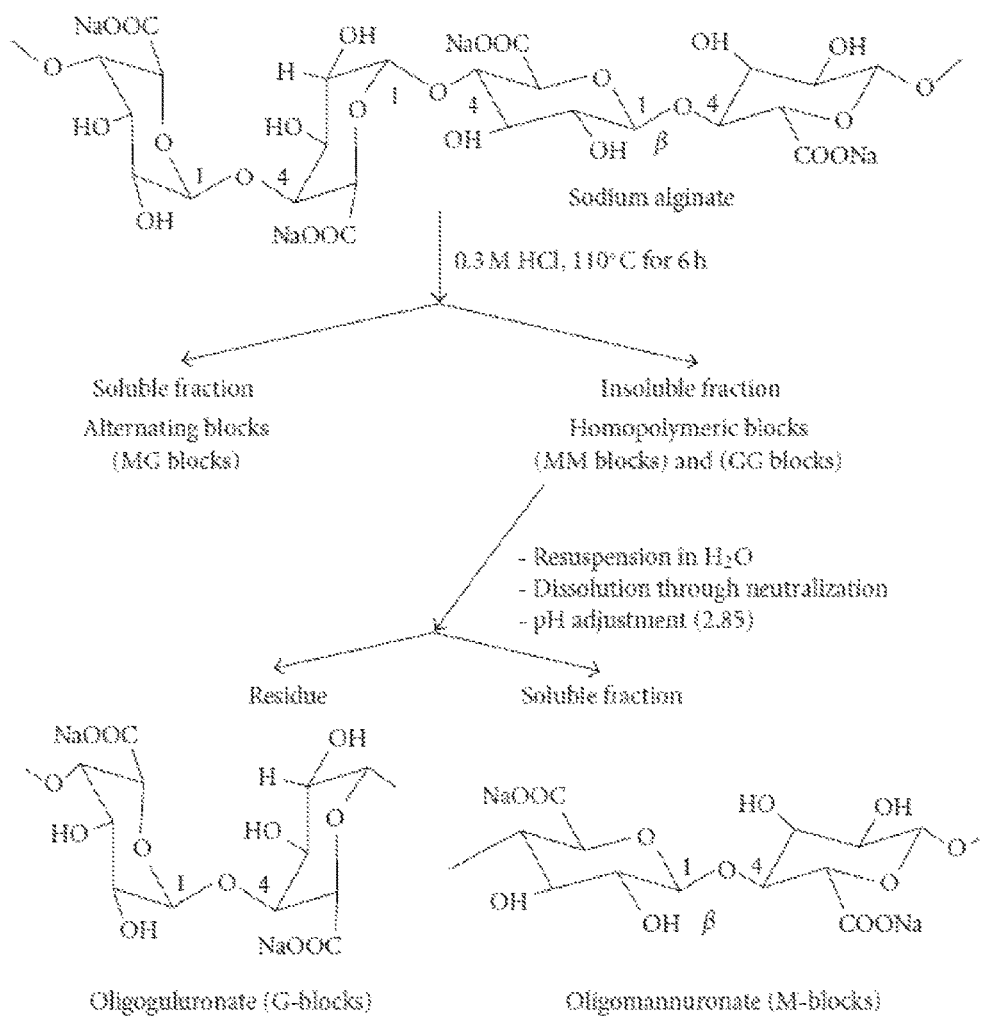
FIG. 9 shows a schematic schematic illustration of the preparation of oligoguluronate blocks (G-blocks).

The oligoguluronate residues (G-blocks) were prepared using a method similar to that described in Huang et al. *Acta Chemica Scandinavica* Vol. 20, pp. 183-190, (1966), and Huang et al. *Carbohydrate Res*. Vol. 32, pp. 217-225 (1974), both of which are incorporated herein by reference. Briefly, sodium alginate (10 g) was dissolved in distilled water and made up to 1 L with 0.3 M HCl. The mixture was then heated at 100° C. for 6 hours. The oligomannuronate and oligoguluronate homopolymeric blocks that remained intact as solid residues were collected via centrifugation for 5 minutes at 4000 rpm, washed, and resuspended in distilled water. The residue was dissolved by the dropwise addition of 0.3 M NaOH. Afterwards, NaCl was added to make up a final concentration of 0.5% (w/v). Ethanol (2 volumes) was added and the resulting precipitate was collected by centrifugation for 5 min at 4000 rpm. The precipitate was then washed and redissolved in water, and the pH was adjusted to 2.85 with 1 M HCl. At this pH value, the oligoguluronate blocks were precipitated and then collected leaving the oligomannuronate blocks in solution. The oligoguluronate fractions were desalted and freeze-dried. A reaction scheme is shown in FIG. 9.

Example 9B—Formulation Properties

Specifically, 0.5% w/v aqueous solution of alignate and G-Block was prepared. Also, a 2% w/v of ciprofloxacin was made by dissolving it in 1% v/v acetic acid solution. A volume of ciprofloxacin was added drop by drop into the solution of alginate, G-block, or a mixture of alginate and G-Block. Meanwhile, homogenization with 15,000 rpm was applied. The whole process was taken in the ice bath. The generated suspension of gel was put overnight, and then was spray dried to collect the dry powder. The composition of the dry powder formulation is shown in the table on the following page.

| Sample code | Ciprofloxacin (C) (mg) | Alginate (A) (mg) | G-block (G) (mg) |
|---|---|---|---|
| 1(C)/0.75(A) + 0(G) | 1 | 0.75 | 0 |
| 1(C)/0.25(A) + 0.5(G) | 1 | 0.25 | 0.5 |
| 1(C)/0(A) + 0.75(G) | 1 | 0 | 0.75 |

Example 9C—SEM Characterization

Figure 10:
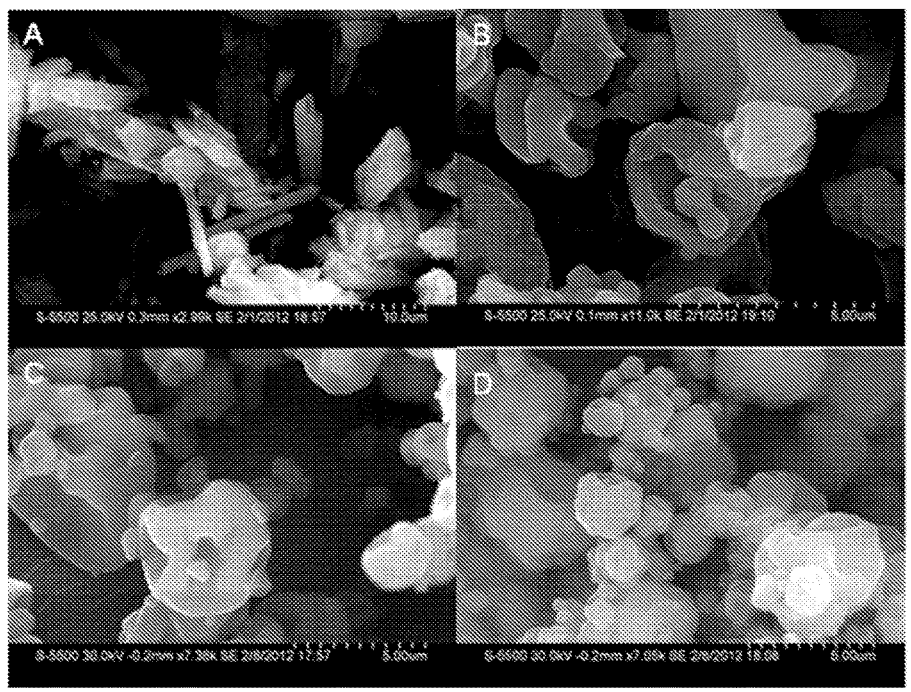
FIG. 10 shows Scanning electron micrographs of: the following (A) ciprofloxacin; (B) 1(C)/0.75(A)+0(G); (C) 1(C)/0.25(A)+0.5(G); and (D) 1(C)/0(A)+0.75(G).

The morphology of the prepared Ciprofloxacin dry powder was examined by SEM (Hitachi S-800 field emission scanning electron microscope operated in second-ary electron mode with a Robinson backscatter detector and with a Hitachi PCI system for digital image capture). Dry particles were mounted on aluminum stubs with double-sided conducting carbon tapes and coated with a 50/50 mixture of Au/Pd to minimize surface charging. The samples were scanned at an accelerating voltage of 20 KV. FIG. 10 shows the SEM for the various particles.

Example 9D—Drug Release

Figure 11:
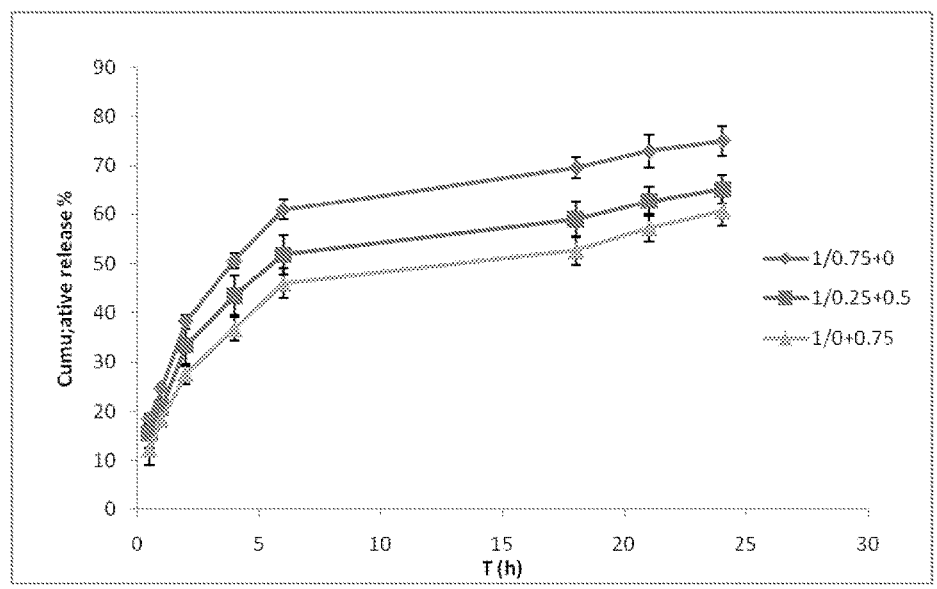
FIG. 11 shows Cumulative release of all dry powder formulations in PBS at 37° C. The upper curve is for 1/0.75+0, the middle curve is for 1/0.25+0.5, and the lower curve is for 1/0+0.75.

The in vitro release pattern of the CF from the developed CF-loaded carrier particles was deter-mined by transferring a certain weight of particles to a vial containing 1.5 ml of PBS, pH 7.4. Samples were maintained at 37° C. with shaking at 100 rpm. At predetermined intervals, 1.2 ml aliquot was withdrawn and analyzed at max of 280 nm using a UV-Vis spectrophotometry. The withdrawn aliquots were replaced with the same volume of fresh buffer, to keep the volume of the release medium constant. The amounts of CF released (µg) from the particles were then calculated using a standard curve of CF in PBS, pH 7.4. Results were expressed as cumulative release (%) relative to the initially loaded weight of CF in the particles. The data points represent average ±SD from three independent experiments. FIG. 11 shows the cumulative release of all dry powder formulations in PBS, at 37° C.

Example 9E—Aerosol Performance

The aerosolization performances of ciprofloxacin dry powder were studied using a Next Generation Impactor (NGI) (MSP Co., Shoreview, Minn.). The prepared 20 mg of powders were filled into a size 3CS capsule (CAPSUGEL®, MA, USA) and placed into an AEROLIZER®. Each capsule was pierced and actuated into the NGI though a stainless steel USP throat adapter at a flow rate of 90/min for 4 s. The powder deposited in the throat, in each dose collection-plate of the NGI, and in the remaining capsule, were each reconstituted with 10 mL of NaOH solution. Powders remaining in the device were washed with 10 mL of NaOH solution. Collected samples were analyzed at max 280 nm using a UV-Vis spectrophotometry. The fine particle fraction (FPF), defined as the total dose of particles with aerodynamic diameters smaller than 5 nm, was calculated via interpolation from the cumulative mass against the cutoff diameter of the respective stages of the NGI. The table below shows NGI data for all formulations.

| Sample code | Fine particle fraction (3-8) % | Fine particle fraction (2-8) % |
|---|---|---|
| 1(C)/0.75(A) + 0(G) | 16.46 | 34.85 |
| 1(C)/0.25(A) + 0.5(G) | 18.14 | 35.04 |
| 1(C)/0(A) + 0.75(G) | 30.11 | 45.25 |

Example 9F—Mucus Transport

Figure 12:
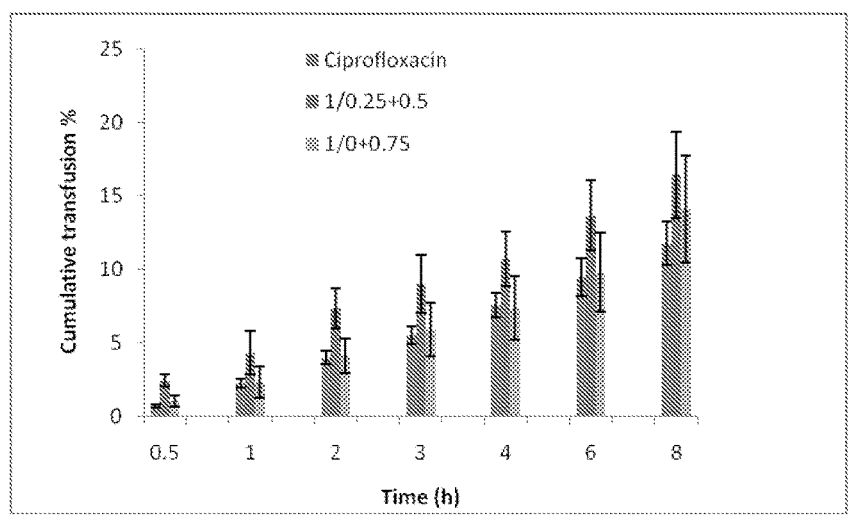
FIG. 12 shows Cumulative transfusion of ciprofloxacin in different dry powder formulations. The left bar in each set is for ciprofloxacin, the middle bar in each set is for 1/0.25+0.5, and the right bar in each set is for 1/0+0.75.

A 20% w/v concentration of type 3 (type 3 M1778-10G, batch 098K7025, Sigma Aldrich, St. Louis, Mo.) was mixed with double distilled water in a shaking incubator overnight. Permeability of ciprofloxacin in different formulations was determined by using a modified diffusion cell setup. The diffusion cell setup consisted of Snapwells inserts that have surface areas of 1.12 cm², that act as the donor side, placed atop 6 well tissue culture plates containing 4.5 mL of PBS buffer as the acceptor side (Corning Snapwells, CLS3802, Corning, N.Y.); Multiwell Primaria 24 well, Falcon, Becton Dickinson Labware, Franklin Lakes, N.J.). Mucus models were plated onto the Snapwells inserts at a volume of 500 µL, which was sufficient to cover the inserts. Particles were applied topically. Samples were removed from the acceptor side at predetermined time points and analyzed at max 280 nm using a UV-Vis spectrophotometry. FIG. 12 shows the cumulative transfusion of ciprofloxacin in different dry powder formulations.

We claim:

1. A solid composition comprising a plurality of hydrogel particles, wherein the hydrogel particles each comprise:
   hydrophilic polymer molecules; and
   a pharmacologically-active agent that treats a disease, disorder, or condition when administered into a subject, the pharmacologically-active agent comprising one or more of amikacin, ciprofloxacin, streptomycin, rifampicin, isoniazid, ethambutol, pyrazinamide, ibuprofen, tobramycin, epinephrine, salbutamol, salmeterol, clenbuterol, levalbuterol, or a pharmaceutically acceptable salt thereof, wherein molecules of the pharmacologically-active agent non-covalently chemically bond with two or more of the hydrophilic polymer molecules to form non-covalent chemical crosslinking between the hydrophilic polymer molecules sufficient to form a hydrophilic polymer matrix without the use of other crosslinking agents.

2. The solid composition of claim 1, wherein one or more of the hydrophilic polymer molecules comprise one or more ionic polymer molecules.

3. The solid composition of claim 1, wherein at least one of the hydrophilic polymer molecules is a PEGylated polymer.

4. The solid composition of claim 2, wherein the hydrogel particles each contain two or more ionic polymers.

5. The solid composition of claim 3, wherein the PEGylated polymer is a PEGylated chitosan, a PEGylated cellulose, or a mixture thereof.

6. The solid composition of claim 1, wherein the hydrophilic polymer molecules comprise one or more non-PEGylated hydrophilic polymers.

7. The solid composition of claim 6, wherein the one or more non-PEGylated hydrophilic polymers comprises one or more of:
   an alginate, a chitosan, a hydroxylated cellulose, a carboxylated cellulose, a mucin, a carrageenan, a hyaluronate, or a mixture thereof.

8. The solid composition of claim 6, wherein the one or more non-PEGylated hydrophilic polymers comprise an alginate or derivatives thereof.

9. The solid composition of claim 2, wherein the one or more ionic polymers comprise at least one cationic polymer and at least one anionic polymer.

10. The solid composition of claim 1, wherein the pharmacologically-active agent is a compound having at least one acidic group, at least one basic group, or at least one acidic group and at least one basic group.

11. The solid composition of claim 10, wherein the pharmacologically-active agent is a compound having at least two acidic groups or at least two basic groups.

12. The solid composition of claim 2, wherein the pharmacologically-active agent forms a pharmaceutically acceptable salt with one or more of the one or more ionic polymers.

13. The solid composition of claim 9, wherein the pharmacologically-active agent has a basic group and an acidic group, and wherein the basic group forms a pharmaceutically acceptable salt with the anionic polymer and the acidic group forms a pharmaceutically acceptable salt with the cationic polymer.

14. A solid composition comprising a plurality of hydrogel particles, wherein the hydrogel particles each comprise:
    a plurality of hydrophilic polymer molecules; and
    a pharmacologically-active agent that treats a disease, disorder, or condition when administered into a subject, the pharmacologically-active agent comprising at least one of ciprofloxacin, tobramycin, or a pharmaceutically acceptable salt thereof, wherein molecules of the pharmacologically-active agent non-covalently chemically bond with two or more of the hydrophilic polymer molecules to form non-covalent chemical crosslinking between the two or more hydrophilic polymer molecules sufficient to form a hydrophilic polymer matrix without the use of other crosslinking agents.

15. The solid composition of claim 1, wherein the non-covalent chemical crosslinking between the pharmacologically-active agent and the hydrophilic polymer molecules that forms the hydrophilic polymer matrix comprises ionic bonding, hydrogen bonding, dipole-dipole interactions, dipole-induced dipole interactions, or dispersion attractions.

16. The solid composition of claim 1, wherein the plurality of hydrogel particles have a mass median aerodynamic diameter of 0.5 to 5.0 µm.

17. The solid composition of claim 1, wherein at least a portion of the hydrophilic polymer molecules comprises a polysaccharide such that at least a portion of the hydrophilic polymer matrix is a polysaccharide matrix.

18. The solid composition of claim 1, wherein the molecules of the pharmacologically-active agent become un-crosslinked with the hydrophilic polymer molecules and are released from the hydrophilic polymer matrix at a specified release rate when the plurality of hydrogel particles are administered into subject.

19. The solid composition of claim 1, wherein the pharmacologically-active agent is administered to treat a disease, disorder, or condition in a human.

20. The solid composition of claim 14, wherein at least one of the plurality of hydrophilic polymer molecules is a PEGylated polymer.

21. The solid composition of claim 20, wherein the PEGylated polymer is a PEGylated chitosan, a PEGylated cellulose, or a mixture thereof.

22. The solid composition of claim 14, wherein at least a portion of the hydrophilic polymer molecules comprises a polysaccharide such that at least a portion of the hydrophilic polymer matrix is a polysaccharide matrix.

23. The solid composition of claim 14, wherein the hydrogel particles each contain two or more hydrophilic polymers.

24. The solid composition of claim 14, wherein the pharmacologically-active agent is a compound having at least one acidic group, at least one basic group, or at least one acidic group and at least one basic group.

25. The solid composition of claim 14, wherein the pharmacologically-active agent forms a pharmaceutically acceptable salt with one or more of the plurality of hydrophilic molecules.

26. The solid composition of claim 14, wherein the plurality of hydrogel particles have a mass median aerodynamic diameter of 0.5 to 5.0 µm.

27. The solid composition of claim 14, wherein the molecules of the pharmacologically-active agent become un-crosslinked with the hydrophilic polymer molecules and are released from the hydrophilic polymer matrix when the plurality of hydrogel particles are administered into the subject.

28. The solid composition of claim 14, wherein the pharmacologically-active agent is administered to treat a disease, disorder, or condition in a human.

29. The solid composition of claim 14, wherein one or more of the hydrophilic polymer molecules comprise one or more ionic polymer molecules.

30. The solid composition of claim 29, wherein the one or more ionic polymers comprise at least one cationic polymer and at least one anionic polymer.

* * * * *